(12) United States Patent
Regnault

(10) Patent No.: US 6,596,004 B1
(45) Date of Patent: Jul. 22, 2003

(54) COMPRESSION DEVICE FOR HAEMOSTASIS OF AN ORGAN SUCH AS THE LIVER

(76) Inventor: Daniel Pierre Regnault, 18 rue Georges Lafenestre, 92340 Bourg-la-Reine (FR)

( * ) Notice: Subject to any disclaimer, the term of this patent is extended or adjusted under 35 U.S.C. 154(b) by 0 days.

(21) Appl. No.: 09/600,494

(22) PCT Filed: Jan. 15, 1999

(86) PCT No.: PCT/IB99/00100

§ 371 (c)(1),
(2), (4) Date: Sep. 21, 2000

(87) PCT Pub. No.: WO99/35976

PCT Pub. Date: Jul. 22, 1999

(30) Foreign Application Priority Data

Jan. 16, 1998 (FR) .............................. 98 00463

(51) Int. Cl.⁷ .............................. A61B 17/08
(52) U.S. Cl. .................................... 606/157
(58) Field of Search .............. 606/157, 139, 606/144, 145, 216, 217

(56) References Cited

U.S. PATENT DOCUMENTS

| 3,130,727 | A | * | 4/1964 | Wood |
| 3,976,079 | A | | 8/1976 | Samuels et al. |
| 4,458,681 | A | * | 7/1984 | Hopkins |
| 5,160,338 | A | | 11/1992 | Vincent |
| 5,797,932 | A | * | 8/1998 | Min et al. |
| 5,843,123 | A | * | 12/1998 | Brazeau |

FOREIGN PATENT DOCUMENTS

| DE | 3831398 A1 | 9/1988 |
| FR | 2650499 | 8/1989 |

* cited by examiner

*Primary Examiner*—Ismael Izaguirre
(74) *Attorney, Agent, or Firm*—Blakely, Sokoloff, Taylor & Zafman

(57) ABSTRACT

The compression device (2) for haemostasis of an organ such as the liver includes at least one flexible strap (4) and at least a connection element (16) for linking one to the other two strap portions extending on opposite sides of the organ. The connection element (16) comprises a thread (18).

18 Claims, 4 Drawing Sheets

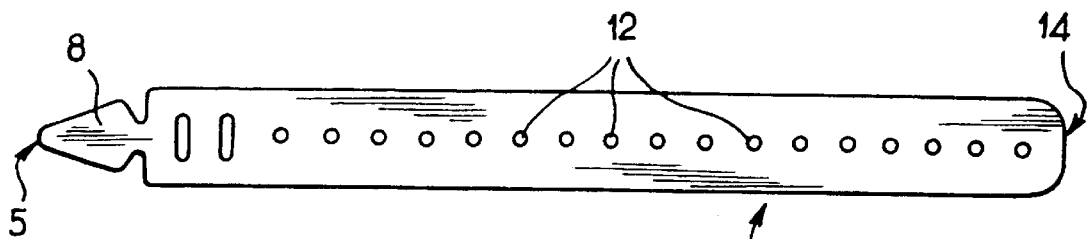
FIG_1
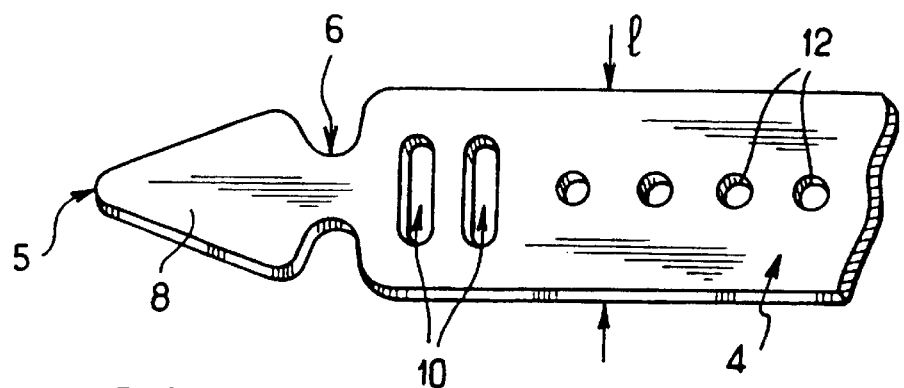
FIG_2
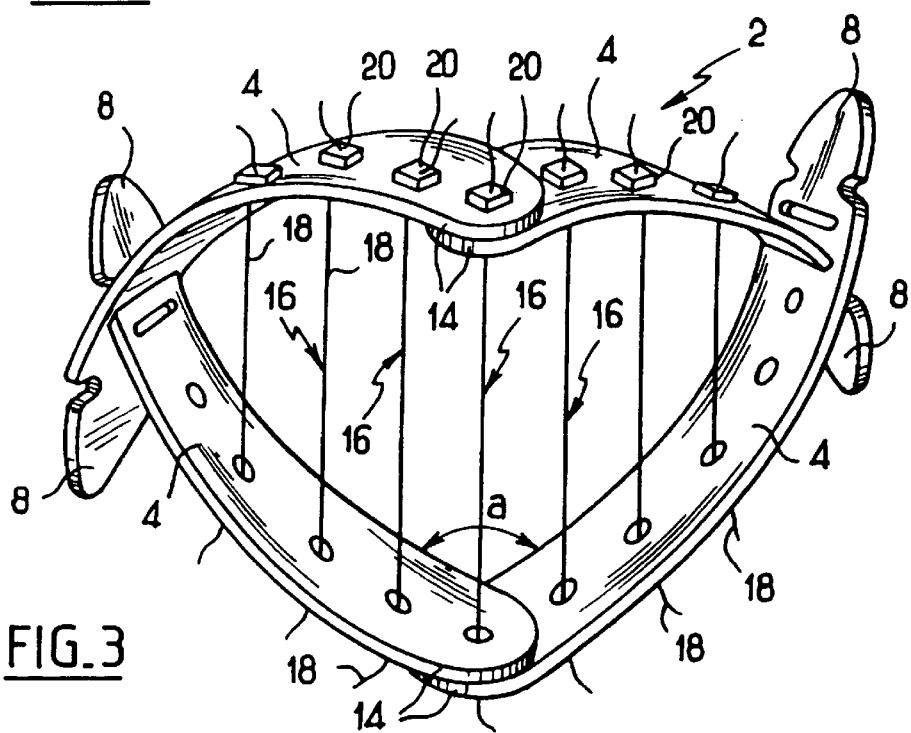
FIG_3

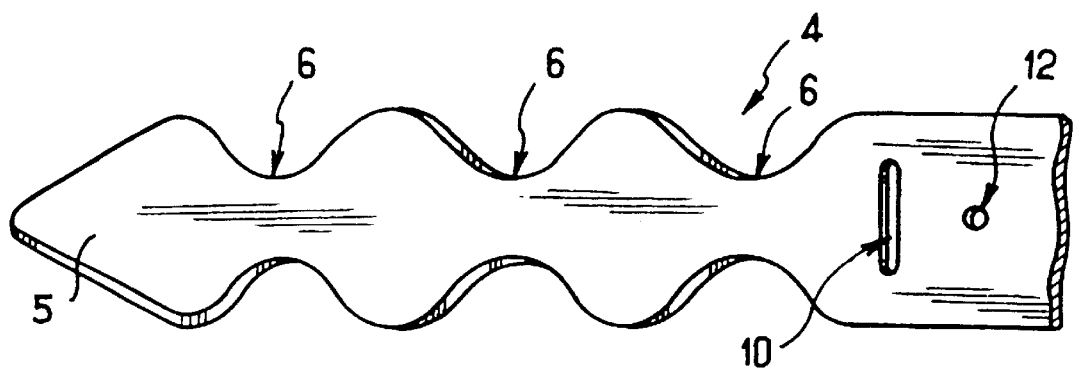
FIG_6
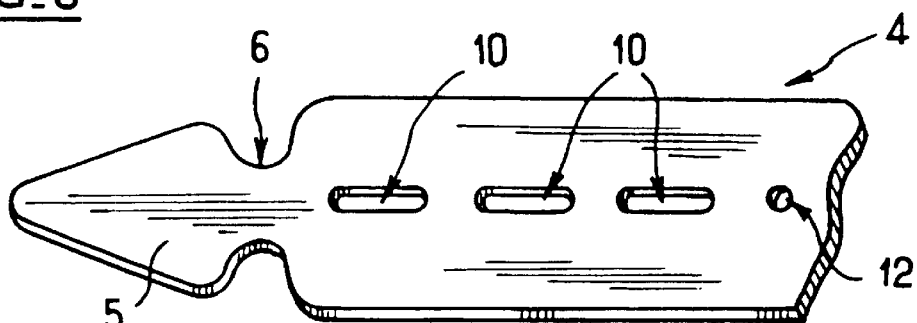
FIG_7
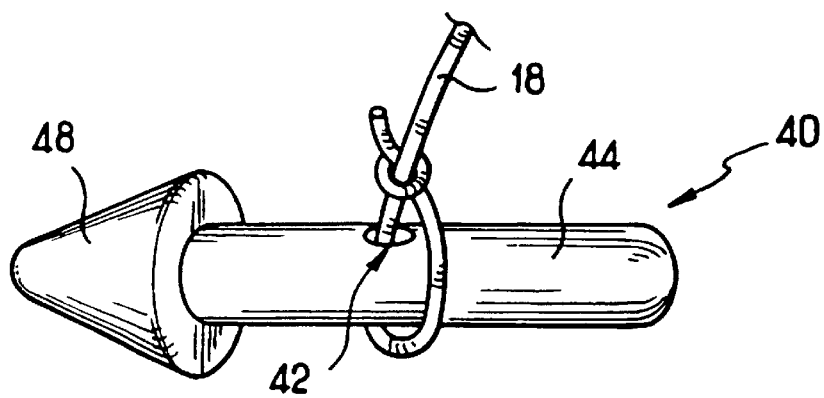
FIG_8
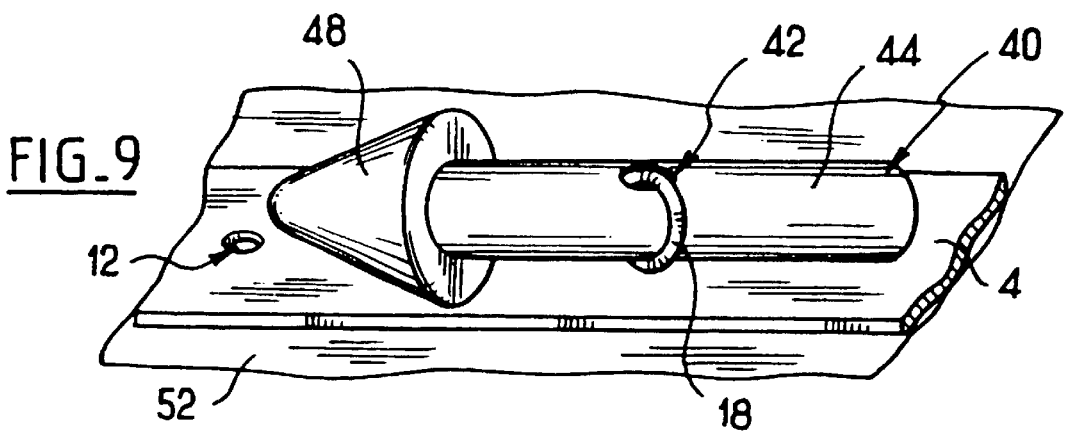
FIG_9

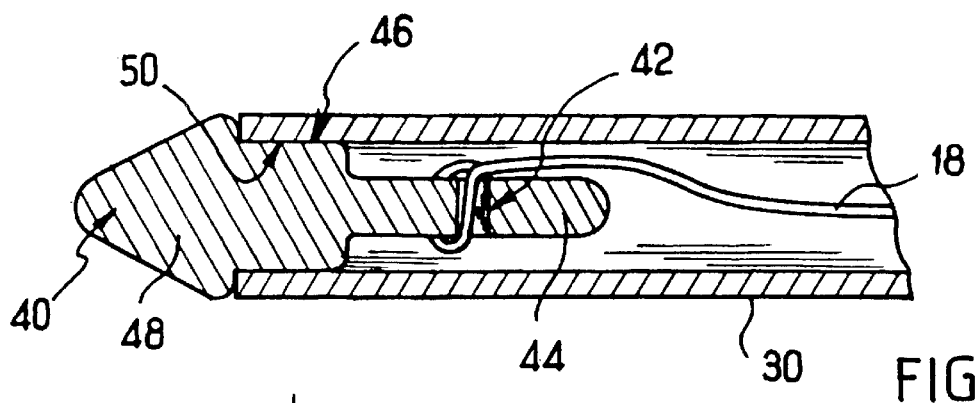
FIG. 10
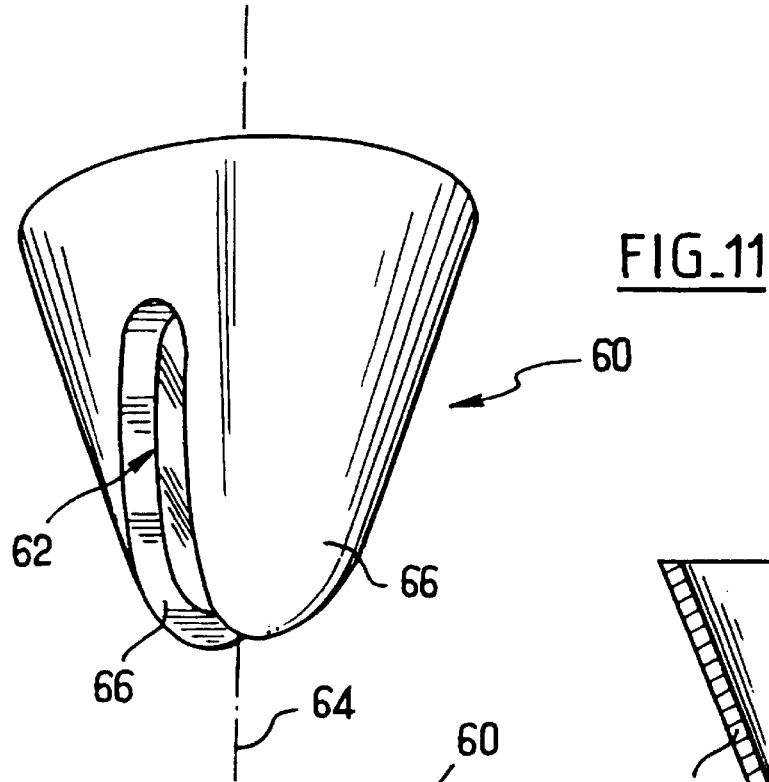
FIG. 11
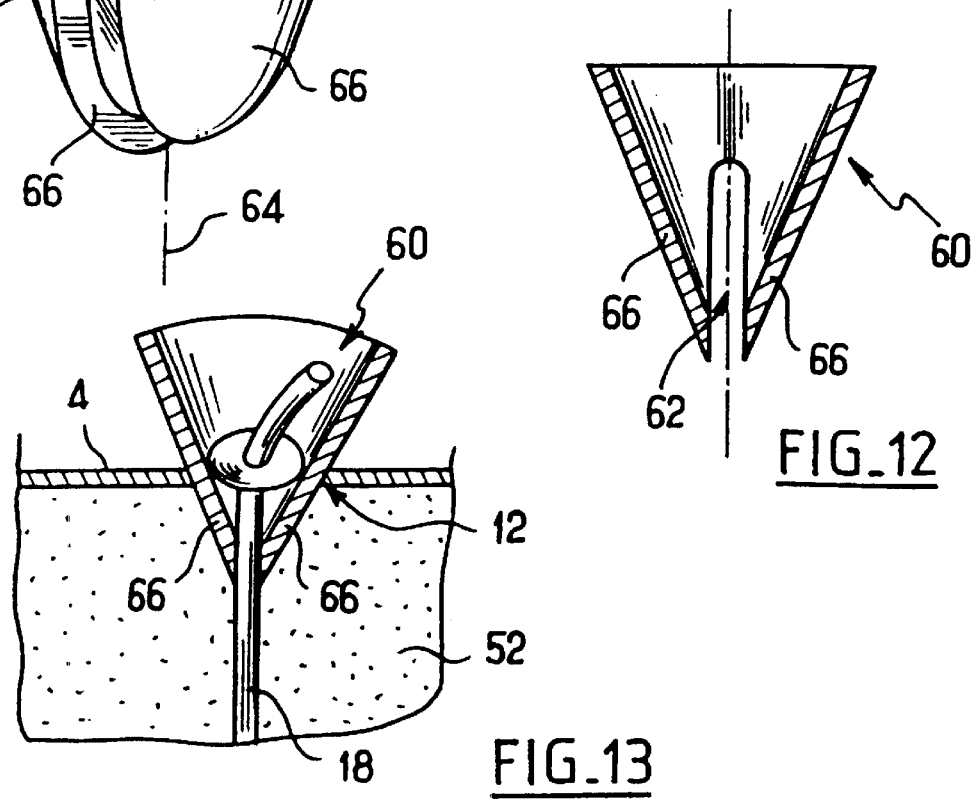
FIG. 12
FIG. 13

COMPRESSION DEVICE FOR HAEMOSTASIS OF AN ORGAN SUCH AS THE LIVER

The present invention relates to the compression devices with which it is possible to effect haemostasis of an organ of the human or animal body, such as the liver, kidney or spleen.

The document FR-2,650,499 discloses al device for haemostasis of the liver, including flexible straps arranged in succession one after the other to form a collar for surrounding part of the liver, and connection rods which are adapted to join facing portions of strap to each other with a view to compressing the liver which is thus surrounded. The rods are fixed by means of a nut engaging with a thread of the rod and bearing externally on the strap portion. This device, which has proved to be of great use, nevertheless has certain disadvantages. The manufacture of the rods and nuts is relatively costly. The size of the device, prior to fitting, is substantial. Moreover, the rigidity of the rods can lead to a shearing effect on the remaining tissues of the organ.

It is an object of the invention to make available a compression device which is less costly to manufacture, is less bulky prior to fitting, can be rendered easily resorbable, and is less aggressive in respect of the organ under haemostasis.

With a view to achieving this object, the invention provides a compression device for haemostasis of an organ such as the liver, including at least one flexible strap and at least one connection element for joining to each other two strap portions extending on both sides of the organ. The connection element comprises a thread.

Thus, before being fitted, the size of the device is reduced. Moreover, the manufacture of the thread is not very costly. The connection element or elements can be rendered rapidly and easily resorbable. The flexibility of the thread allows it to adapt to the configurations of the organ without being aggressive thereto.

The strap advantageously has at least one orifice, the device including at least one fixing element adapted to be fixed to the thread and dimensioned in such a way that it cannot pass through the orifice.

Thus, the connection between the thread and the strap is ensured in a manner which is particularly simple to implement during a surgical intervention.

The fixing element is advantageously adapted to clamp the thread.

Advantageously, the fixing element is adapted to receive the thread and to rest upon the orifice to stretch the thread.

Advantageously, the fixing element has a generally conical, hollow shape and is opened at a tip of the cone.

Advantageously, the fixing element is provided with a notch extending from the tip of the cone.

The device advantageously includes an insertion element adapted to be fixed to the thread, and a thread feeder having one end adapted to receive the insertion element.

Thus, the thread can be introduced quickly and simply into the organ which is to be compressed.

Advantageously, the end of the thread feeder being a first end, the thread feeder is hollow and has a second end, the two ends being open.

The thread can thus be accommodated in the thread feeder.

Advantageously, the insertion element includes the fixing element.

The strap advantageously has at least one notch and at least one orifice adapted to receive the strap or an identical strap in the area of the notch, prohibiting its withdrawal from the orifice.

A simple means is thus provided for joining two strap portions directly to each other.

The strap advantageously has a pointed end adjacent to the notch.

The device advantageously includes at least one pair of straps joined to each other directly, and joined to each other via the connection element or elements.

Advantageously, the pair being a first pair, it includes a second pair of straps joined to each other directly, the connection element joining the straps of the first pair to the straps of the second pair The thread is advantageously single-stranded.

In an alternative and also advantageous version, it can be braided.

The thread is advantageously resorbable.

The invention also provides a method for fitting a compression device according to the invention, including the thread feeder and the four straps, the method comprising the steps of:

introducing the thread feeder, equipped with the thread, through one strap of each pair, then through the organ to be compressed, then through another, strap of each pair;

introducing at least one other connection element through the organ so that this other element joins two straps of one of the pairs to each other; and extracting the thread feeder from the organ, leaving the thread in the organ.

Thus, the thread feeder forms a hinge between the two pairs of straps in order to render them movable in rotation relative to each other, with a view to modifying the configuration of the device during the surgical intervention and adapting it to that of the organ Other characteristics and advantages of the invention will be evident from the following description of a preferred embodiment given by way of nonlimiting example. In the attached drawings:

FIG. 1 is a view of a strap of the device according to a preferred embodiment of the invention;

FIG. 2 is a view, on a larger scale, of a detail from FIG. 1;

FIG. 3 is a perspective view of the device in the fitted state, the organ not being represented;

FIGS. 6 and 7 are two views similar to FIG. 1 showing two alternative embodiments of the straps;

FIG. 8 is a perspective view of an alternative embodiment of the fixing element connected to a thread;

FIG. 9 is a partial perspective view of the fixing element according to FIG. 8 in position on the organ;

FIG. 10 is a cross-sectional of the fixing element of the FIG. 8 received in a thread feeder;

FIGS. 11, 12 and 13 are views respectively in perspective and in axial cross-section before and after fitting on the organ, of an alternative embodiment of the fixing element.

Figure 4:
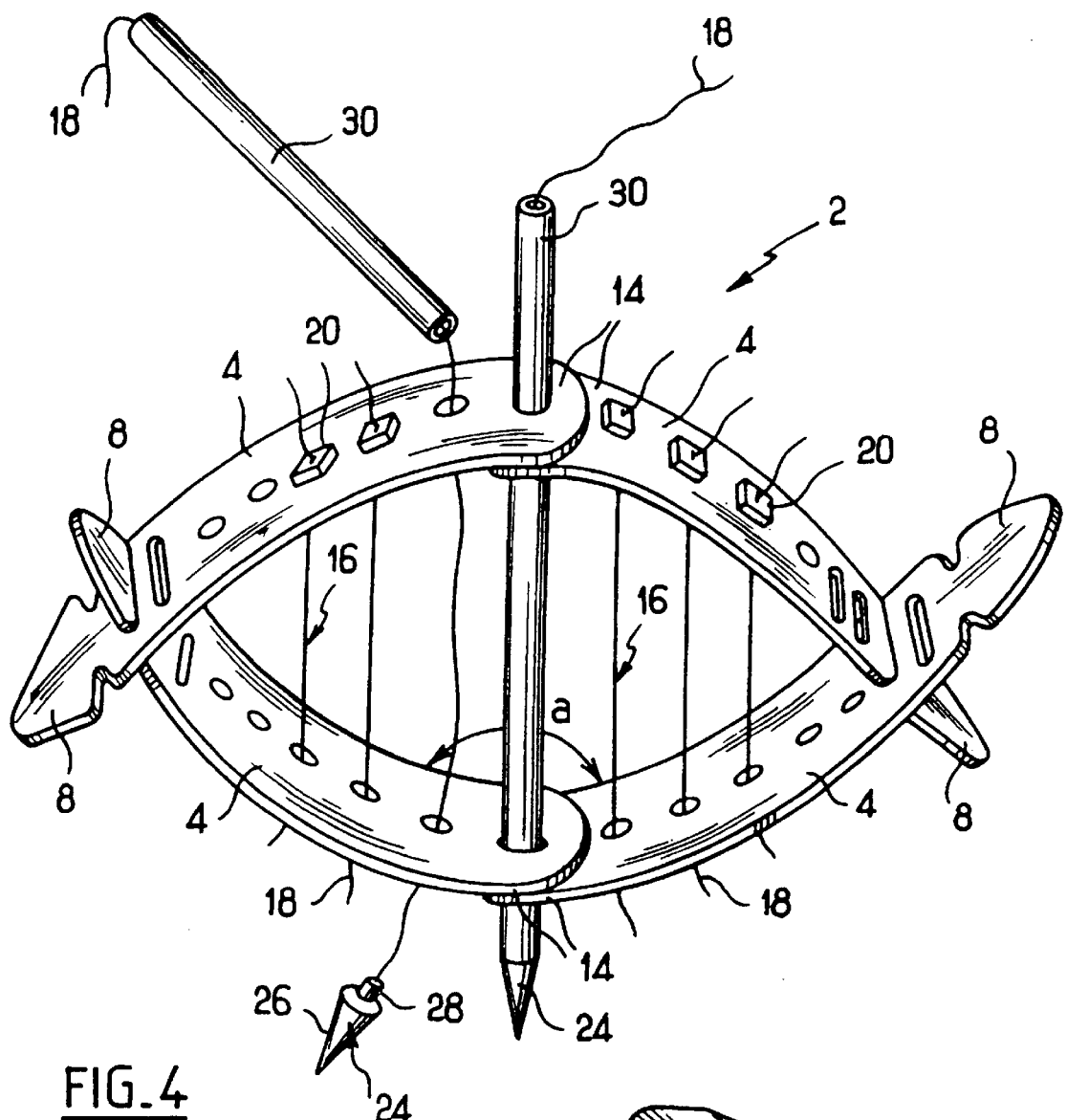
FIG. 4 is a view, analogous to FIG. 3, illustrating a step in fitting the device on the organ.

The present embodiment of the compression device according to the invention for haemostasis of an organ of the human or animal body, such as the liver, kidney or spleen, is represented in FIG. 3. The device 2 here includes four semi-rigid, flexible straps 4 illustrated in FIGS. 1 and 2.

Each flexible strap 4 is of a generally flat, elongate and rectangular shape in plan view, with a width 1 which is substantially constant. Near one longitudinal end 5, it has a narrowing of its width defining a notch 6. The strap has a portion of a generally pointed triangular shape 8 extending from the notch 6, situated at the base of the triangle, as far as the point situated at the end 5 of the strap. This pointed portion 8 has a width decreasing from its base towards the point. The base has a width smaller than the width 1 of the rest of the strap, but greater than the width of the notch 6.

The strap 4 has oblong orifices 10, for example two in number, arranged near the notch 6, at a short distance from the pointed portion 8, the length of the oblong orifices 10 extending along the width of the strap. The length of the oblong orifices 110 is greater than the width of the notch 6 for the purpose of receiving the latter or an identical notch, and is smaller than the width of the base of the pointed portion The strap 4 has several circular orifices 12 identical to each other, arranged along the longitudinal axis of the strap, from the oblong orifices 10 towards a second longitudinal end 14 of the strap. The length of the strap is, for example, between 15 and 20 cm. Its width 1 is, for example, between 1 and 2 cm.

Figure 5:
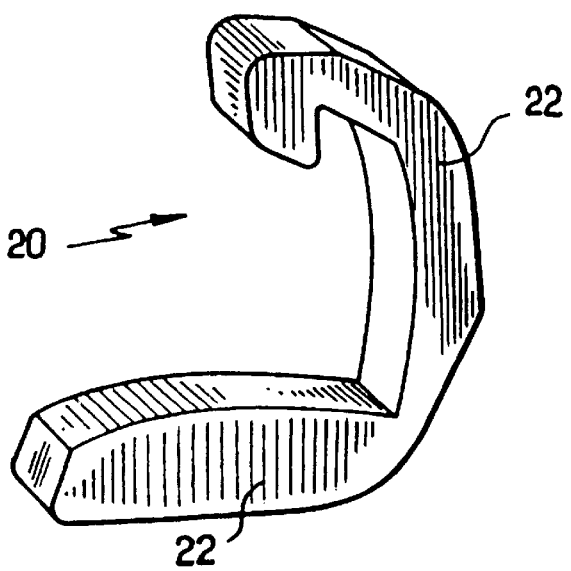
FIG. 5 is a diagrammatic perspective view of a clip of the device in FIG. 3.

The device includes connection elements 16 each comprising a section of resorbable thread 18, braided or single-stranded, as well as two fixing elements, in this case formed by clips 20, such as the one in FIG. 5. Each clip 20 is, for example, made in one piece and has two flexible brackets 22 articulated on one another with a view to clamping the thread 18 between the two brackets. The dimensions of the clip 20 are chosen so that it cannot pass through the circular orifices 12 of the strap. The clip 20 will, for example, be off the same type as one of the resorbable clips marketed under the name Absolok® by Ethicon Endosurgery, or a clip of the type described in application EP-0,086,640.

In order to fit the device on an organ on which haemostasis is to be effected, the device additionally comprises one or more insertion elements, each made up in this case of a nose cone 24 generally symmetrical in revolution about its axis, similar to that of a spinning top. It has a front part 26 of a generally conical shape which widens away from a pointed front end, and a cylindrical rear part 28 which has a diameter smaller than the greatest diameter of the front part 26. The rear part 28 is intended to allow the end of the thread 18 to be fixed thereto. It has, for example, an orifice in which the thread 18 can be introduced in order to make a knot around this rear part 28. Alternatively, the thread will be able to be crimped in an orifice of the rear part of the nose cone.

For fitting purposes, the device additionally includes one or more thread feeders 30 comprising a hollow, rectilinear cylindrical tube which is open at its two axial ends. The internal diameter of one of the axial ends is adapted to correspond to that of the rear part 28 of the nose cone 24 with a view to mounting this rear part on the end of the thread feeder 30 and thereby to receive the nose cone on the thread feeder, the thread 18 then extending through the thread feeder 30 and emerging at the other axial end. The thread feeder 30 will have an external diameter which is smaller than that of the orifices 12 and, for example, between 1.5 and 2 mm, and a length of between 15 and 20 cm. The thread 18 will preferably have a diameter of less than 1 mm.

During a surgical intervention, the device 2 can be fitted on the organ using the following method.

The straps 4 are arranged in two pairs. In each pair, the pointed portion 8 of one of the straps 4 is introduced into an oblong orifice 10 of the other strap. The oblong orifice 10 thus secures the pointed portion 8 against inadvertently coming loose. The straps 4 are then arranged in a collar around the organ, as in FIG. 4, in such a way that the second longitudinal ends 114 of the straps of each pair overlap in pairs. Two ends 14 are on one side of the organ, and the other two ends 14 are on the other side.

The nose cone 24 being mounted on the thread feeder 30 as mentioned above, two circular orifices 12 of two ends 14 coincide and overlap, and the nose cone and the thread feeder are introduced into these two orifices. The nose cone 24 and the thread feeder 30 are then pushed through the organ in the direction of the other two ends 14, the front conical shape of the nose cone 24 facilitating this introduction. The nose cone and the thread feeder then open out into two coincident orifices 12 of the two other overlapping ends 14 and pass through these. The thread feeder and the nose cone at the centre of the device are then in the configuration in FIG. 4. The thread feeder 30 extends through the organ and in four respective circular orifices 12 of the ends 14 of the four straps. The thread feeder and the nose cone are left for the time being in this configuration.

Another connection element 16 is then put into place in the following way. With the aid of another nose cone 24 mounted on another thread feeder 30 as before, the nose cone and the thread feeder are introduced into a circular orifice 12 of a strap 4 of one of the pairs, then into the organ, then into the other strap 4 of the same pair, in a circular orifice 12 thereof in line with the associated circular orifice. When the nose cone 24 has passed through this other strap, the nose cone 24 is removed from the thread feeder 30. While holding the nose cone, the thread feeder is made to pass through in the opposite direction so that it emerges from the organ via the side through which it entered, the thread feeder following the thread 18 which passes through it, until the thread feeder 30 is withdrawn from the straps 4 and from the organ, as is illustrated in FIG. 4. The thread 18 is then cut between the thread feeder 30 and the nearest strap 4 in order to release the thread feeder. A clip 20 is mounted on the section of cut thread 18 adjacent to the strap 4, by clamping the clip over the thread. The clip 20 bears against the associated circular orifice 12, on an external face of the strap 4 opposite the organ. Similarly, the nose cone 24 is separated from the thread 18, and another clip 20 is fitted on the associated end of the thread 18, this clip also bearing against the corresponding strap 4. The clips 20 are fitted in such a way as to ensure the desired compression of the organ by means of the thread 18 and the straps 4, the thread being subjected to a tensile stress. The connection element 16 is thus fitted as illustrated in FIGS. 3 and 4. Other connection elements 16 are fitted in the same way. It will be advantageous, prior to the intervention, to have mounted a respective nose cone on each of the connection elements to be fitted.

When necessary, it is possible to modify the angular position of one of the pairs of straps 4 in relation to the other pair by turning the pairs around the central thread feeder 30 still in place. Thus, in FIG. 4, the two pairs of straps form an angle a of about 180°, whereas this angle a is only 90° in FIG. 3.

When all the other connection elements 16 have been fitted, it is possible to finish fitting the first connection element associated with the thread feeder 30 in place. To do this, the nose cone 24 and the thread feeder 30 are separated, the latter is extracted, and the clips 20 are mounted. At any time during the fitting of the device 2 on the organ, it is possible to modify the direct fixing to each other of the straps 4 of each pair by changing the oblong orifice 10 in which the pointed part 8 is engaged.

The straps 4 will preferably be made of an resorbable material.

It will be possible to provide pointed portions 8 and/or oblong orifices 10 at both longitudinal ends of each strap.

The device will thus be able to be shaped into a collar by means of only two straps whose longitudinal ends 5, 14 are directly fixed to one another. It will also be possible to provide a single strap which is curved in a loop, and two portions of which are fixed directly to each other. The number of straps in the device can be greater than four, according to the anatomy and the volume of the organ being operated on.

It will be possible to vary the number and the arrangement of the oblong orifices 10 and the circular orifices 12.

It has been illustrated on FIGS. 6 and 7 two alternative embodiments of the strap 4. On FIG. 6, the strap 4 has near the end 5, a plurality of narrowings of its width defining a same number of successive notches 6. On FIG. 7, the oblong orifices 10 extend parallely to the length of the strap, one following the other. Once the strap is introduced in such an orifice, it is only necessary to rotate the strap for a quarter of turn to forbid its withdrawal. Preferentially the strap combines the features of these two figures.

In reference to FIGS. 8 to 10, in the embodiment illustrated, the nose cone 40 or insertion element is also fixing element. It has at mid-length an orifice 42 extending in the rear portion 44, perpendicularly to its axis. This orifice 42 opens out at its two ends to receive a suture thread 18 connected to itself in a loop. The other features of the nose cone 40 are identical to those of the nose cone 24 described above. Moreover the nose cone 40 has a length greater than the diameter of the orifices 12, preferentially highly greater to this diameter, for example, a length equals to four or five times this diameter. To facilitate the temporary fixing of the nose cone 40 to the thread feeder 30, it is possible to provide a shoulder 46 adjacent to the rear portion 44 and to the front portion 48 of the nose cone. This shoulder 46 is only illustrated on FIG. 10. For passing through the organ subject to haemostasis, the nose cone 40 is fixed to an end of thread feeder 30 in which it is engaged. This connection is operated by friction between the internal surface 50 of the thread feeder and the shoulder 46. This shoulder preserves at the rear portion of the nose cone 40 the volume for receiving the thread 18 in the thread feeder.

Contrarily to the nose cone 24 above described, the nose cone 40 may be used as fixing element. Indeed, after the nose cone 40 has been passed through the organ 52 with the thread feeder 30, the nose cone may be separated from the thread feeder and the thread feeder may be withdrawn from the organ 52. Then, a traction upon the thread 18 from the side of the organ 52 opposite to the nose cone applies the nose cone against the associated strap 4 and the orifice 12, as illustrated on FIG. 9. As the nose cone is placed laterally against the orifice, its length does not allow it to pass through the orifice. This end of the thread is consequently jammed. Once again, the nose cone may be realized in a resorbable material.

An alternative embodiment of the fixing clip 20 of FIG. 5 is illustrated in FIG. 11. The fixing element 60 according to this embodiment has a conical hollow shape. This cone has two grooves or notches 62 extending one in face of the other on both sides of an axis 64 of the cone and joining at its tip to provide an orifice. The grooves 62 form two brackets 66 having rounded points extending one in face of the other. The cone is made from a soft and resorbable material so that the two brackets 66 are flexible one towards the other. To clamp an end of the thread 18 on one side of the organ 52, the cone 60 is placed on this end of the thread, the point of the cone being on the side of the orifice 12, and then a knot is made on the thread 18 upon the position of the thread extending in the cone. The point of the cone 60 is introduced in the orifice 12. Due to the solicitation by the walls of the orifice, the brackets 66 contract one towards the other. Due to the traction upon the thread, the knot is introduced into the cone and then bears on the inside of the brackets 66, so that these ones forbid further progressing of the knot. The end of the thread 18 and the cone 60 are thus clamped by way of a wedge-effect.

The notches 62 are equivalent to removal of material and provide two brackets 66 extending at rest at interval one from the other. The notches 62 may be replaced by two slots defining two brackets extending at rest one against the other.

What is claimed is:

1. Compression device (2) for haemostasis of an organ, including at least one flexible strap (4) and at least a connection element (16) for linking one to the other two strap portions extending on opposite sides of the organ, characterized in that the connection element (16) comprises a thread (18), also characterized in that the strap (4) has at least one orifice (12), the device including at least one fixing element (20; 40; 60) adapted to be fixed to the thread (18) and dimensioned in such a way that it cannot pass through the orifice (12).

2. Device according to claim 1, characterized in that the fixing element (20; 60) is adapted to clamp the thread (18).

3. Device according to claim 1 or 2, characterized in that the fixing element (60) is adapted to receive the thread (18) and to rest upon the orifice (12) to stretch the thread.

4. Device according to one of claims 1 or 2, characterized in that the fixing element (60) has a generally conical hollow shape and is opened at a tip of the cone.

5. Device according to claim 4, characterized in that the fixing element (60) is provided with a notch (62) extending from the tip of the cone.

6. Device according to claim 1, characterized in that it includes an insertion element (24; 40) adapted to be fixed to the thread (18), and a thread feeder (30) having one end adapted to receive the insertion element (24; 40).

7. Device according to claim 6, characterized in that the end of the thread feeder (30) being a first end, the thread feeder is hollow and has a second end, the two ends being open.

8. Device according to one of claims 6 or 7, characterized in that the insertion element (40) includes the fixing element.

9. Device according to any one of claims 1 or 2, characterized in that the strap has at least one notch (6) and at least one orifice (10) adapted to receive the strap or an identical strap (4) in the area of the notch (6), prohibiting its withdrawal from the orifice (10).

10. Device according to claim 9, characterized in that the strap (4) has a pointed end (8) adjacent to the notch (6).

11. Device according to any one of claim 1, characterized in that it includes at least one pair of straps (4) joined to each other directly, and joined to each other via the connection element or elements (16).

12. Device according to claim 11, characterized in that the pair being a first pair, it includes a second pair of straps (4) joined to each other directly, the connection element (16) joining the straps (4) of the first pair to the straps (4) of the second pair.

13. Device according to any one of claims 1 or 2, characterized in that the thread (18) is resorbable.

14. Device according to any one of claims 1 or 2, characterized in that the thread (18) is resorbable.

15. Method for fitting a compression device, including a thread feeder and two pairs straps, the method comprising the steps of:

introducing the thread feeder, equipped with a thread, through one strap of a first pair of straps, then through an organ to be compressed, and then through another strap of the first pair;

introducing at least one other connection element through the organ so that this other element joins two straps of at least one of the first and second pairs of straps to each other; and extracting the thread feeder from the organ, leaving the thread in the organ.

16. Method according to claim 15, further comprising the step of moving the first and second pairs of straps relative to each other in rotation around a hinge formed by a thread feeder, to modify the configuration of the device.

17. Compression device (2) for haemostasis of an organ, including at least one flexible strap (4) and at least a connection element (16) for linking one to the other two strap portions extending on opposite sides of the organ, characterized in that the connection element (16) comprises a thread (18), and further characterized in that the device includes an insertion element (24; 40) adapted to be fixed to the thread (18), and a thread feeder (30) having one end adapted to receive the insertion element (24; 40).

18. Compression device (2) for haemostasis of an organ, including at least one flexible trap (4) and at least a connection element (16) for linking one to the other two strap portions extending on opposite sides of the organ, characterized in that the connection element (16) comprises a thread (18), and characterized in that the device includes at least one pair of straps (4) joined to each other directly, and joined to each other via the connection element or elements (16).

* * * * *

UNITED STATES PATENT AND TRADEMARK OFFICE
CERTIFICATE OF CORRECTION

PATENT NO. : 6,596,004 B1
DATED : July 22, 2003
INVENTOR(S) : Rignault

It is certified that error appears in the above-identified patent and that said Letters Patent is hereby corrected as shown below:

Title page,
Item [76], Inventor, please delete "Regnault" and insert -- Rignault --.

Signed and Sealed this

Seventh Day of September, 2004

JON W. DUDAS
*Director of the United States Patent and Trademark Office*